(12) United States Patent
Peter (10) Patent No.: US 10,150,960 B2
(45) Date of Patent: Dec. 11, 2018

(54) C-PROBE LIBRARIES FOR DNA TARGET ENRICHMENT

(71) Applicant: Agilent Technologies, Inc., Loveland, CO (US)

(72) Inventor: Brian Jon Peter, Loveland, CO (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 1021 days.

(21) Appl. No.: 13/777,842

(22) Filed: Feb. 26, 2013

(65) Prior Publication Data

US 2014/0242577 A1 Aug. 28, 2014

(51) Int. Cl.
| | |
|---|---|
| *C12Q 1/68* | (2018.01) |
| *C12N 9/00* | (2006.01) |
| *C07H 21/04* | (2006.01) |
| *C12N 15/10* | (2006.01) |

(52) U.S. Cl.
CPC .................................. *C12N 15/10* (2013.01)

(58) Field of Classification Search
None
See application file for complete search history.

(56) References Cited

U.S. PATENT DOCUMENTS

| | | | | |
|---|---|---|---|---|
| 7,108,976 B2* | 9/2006 | Jones | .................... | C12Q 1/6809 435/6.12 |
| 2011/0269631 A1* | 11/2011 | Fu et al. | ............................ | 506/2 |

OTHER PUBLICATIONS

"How many species of bacteria are there?" WiseGeek.com, accessed Jan. 21, 2014.*
"List of sequenced bacterial genomes" Wikipedia.com; accessed Jan. 24, 2014.*
Chase and Richardson, "Exonuclease VII of *Escherichia coli*," The Journal of Biological Chemistry, vol. 249, No. 14, Jul. 25, 1974, pp. 4553-4561.*
"Multiplex amplification of large sets of human exons," Porreca et al., Nature Methods, vol. 4, No. 11, Nov. 2007, pp. 931-936.*
Akhras, et al., "Connector Inversion Probe Technology: A Powerful One-Primer Multiplex DNA Amplification System for Numerous Scientific Applications.", PLoS One, Sep. 19, 2007;2(9):e915.
Dahl, et al. "Multigene amplification and massively parallel sequencing for cancer mutation discovery.", PNAS, May 29, 2007, vol. 104, No. 22, pp. 9387-9392.
Dahl, et al. "Multiplex amplification enabled by selective circularization of large sets of genomic DNA fragments.", Nucleic Acids Research, 2005, vol. 33, No. 8.
Howell, et al., "Glycosylases and AP-cleaving enzymes as a general tool for probe-directed cleavage of ssDNA targets.", Nucleic Acids Research, 2010, vol. 38, No. 7.
Isaksson, et al., "MLGA—a rapid and cost-efficient assay for gene copy-number analysis.", Nucleic Acids Research, 2007, vol. 35, No. 17.
Larsson, et al., "In situ genotyping individual DNA molecules by target-primed rolling-circle amplification of padlock probes.", Nature Methods, vol. 1, No. 3 | Dec. 2004, pp. 227-232.
Porreca, et al., "Multiplex amplification of large sets of human exons.", Nature Methods, Oct. 2007, pp. 1-6.

* cited by examiner

*Primary Examiner* — Bradley L. Sisson (57) ABSTRACT

Provided herein is a method for enriching a target nucleic acid molecule. In one embodiment, the method may involve hybridizing a C-probe to a strand of a target nucleic acid to produce a complex, enzymatically removing any 3' overhanging end from the target nucleic acid of the complex to produce a 3' hydroxyl group at the 3' end; extending the 3' end of the first sequence using the oligonucleotide sequence of the C-probe as a template; enzymatically removing any 5' overhanging end from the target nucleic acid, either before or after the extending step, to produce an 5' phosphate group at the end of the second sequence; and ligating the 5' phosphate group at the end of the second sequence to the 3' hydroxyl group at the end of the first sequence to produce a circular DNA molecule that contains the target sequence and the complement of the oligonucleotide sequence.

20 Claims, 7 Drawing Sheets

C-PROBE LIBRARIES FOR DNA TARGET ENRICHMENT

BACKGROUND

Methods for genome partitioning, i.e., separating selected regions of a genome from other regions, find use in a variety of genomic analysis applications, including, but not limited to SNP analysis, sequencing, mutation detection and the detection of chromosomal rearrangements. This disclosure relates, in part, to a method for genome partitioning.

SUMMARY

Provided herein is a method for processing a nucleic acid. In certain embodiments, the method may comprise: (a) hybridizing a C-probe to a strand of a target nucleic acid to produce a complex, wherein: (i) the strand comprises a target sequence that is flanked by a first sequence and a second sequence, and (ii) the C-probe comprises a first region that hybridizes to the first sequence, a second region that hybridizes to the second sequence, and an oligonucleotide sequence between the first and second regions; (b) enzymatically removing any 3' overhanging end from the target nucleic acid of the complex to produce a 3' hydroxyl group at the 3' end of the first sequence; (c) extending the 3' end of the first sequence using the oligonucleotide sequence of the C-probe as a template, wherein the extending results in a 3' hydroxyl group that is adjacent to the 5' end of the second sequence; (d) enzymatically removing any 5' overhanging end from the target nucleic acid, either before or after the extending of step (c), to produce an 5' phosphate group at the end of the second sequence; and (e) ligating the 5' phosphate group at the end of the second sequence to the 3' hydroxyl group at the end of the first sequence to produce a circular DNA molecule that contains the target sequence and the complement of the oligonucleotide sequence. A kit for performing the method is also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "nucleic acid sample," as used herein denotes a sample containing nucleic acids. A nucleic acid samples used herein may be complex in that they contain multiple different molecules that contain sequences. Genomic DNA samples from a mammal (e.g., mouse or human) are types of complex samples. Complex samples may have more then $10^4$, $10^5$, $10^6$ or $10^7$ different nucleic acid molecules. A DNA target may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "target polynucleotide," as use herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "partitioning", with respect to a genome, refers to the separation of one part of the genome from the remainder of the genome to produce a product that is isolated from the remainder of the genome. The term "partitioning" encompasses enriching.

The term "genomic region", as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "genomic sequence", as used herein, refers to a sequence that occurs in a genome.

The term "genomic fragment", as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adaptor ligated (in which case it has an adaptor ligated to one or both ends of the fragment), or non-adaptor ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains to binding sites for sequences in the oligonucleotide.

The term "affinity tag", as used herein, refers to moiety that can be used to separate a molecule to which the affinity tag is attached from other molecules that do not contain the affinity tag. An "affinity tag" is a member of a specific binding pair, i.e. two molecules where one of the molecules through chemical or physical means specifically binds to the other molecule. The complementary member of the specific binding pair, referred to herein as a "capture agent" may be immobilized (e.g., to a chromatography support, a bead or a planar surface) to produce an affinity chromatography support that specifically binds the affinity tag. In other words, an "affinity tag" may bind to a "capture agent", where the affinity tag specifically binds to the capture agent, thereby facilitating the separation of the molecule to which the affinity tag is attached from other molecules that do not contain the affinity tag.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -$PEG_n$-Biotin where n is 3-12.

The term "terminal nucleotide", as used herein, refers to the nucleotide at either the 5' or the 3' end of a nucleic acid strand. The nucleic acid strand may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by enzyme such as an exonuclease or endonuclease. In order to digest a nucleic acid, an enzyme and a nucleic acid are contacted under conditions suitable for the enzyme to work. Conditions suitable for activity of commercially available enzymes, e.g., restriction enzymes and exonuclease, are known, and supplied with those enzymes upon purchase.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "separating", as used herein, refers to physical separation of two elements (e.g., by size or affinity, etc.) as well as degradation of one element, leaving the other intact.

The term "target sequence" refers to a sequence that is in an unmodified genome, as well as genomes that have been modified (e.g., fragmented and/or adaptor-ligated) or copied. An oligonucleotide that hybridizes to a target genomic sequence base-pairs with the genome sequence. A genomic fragment that contains a target sequence may be in the range of 0.1 kb in length to over 500 kb in length or more, e.g., 0.5 kb to 10 kb or 5 kb to 100 kb, for example.

The term "reference chromosomal region," as used herein refers to a chromosomal region of known genotype, e.g., of known nucleotide sequence.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The term "genotyping", as used herein, refers to any type of analysis of a nucleic acid sequence, and includes sequencing, polymorphism (SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of a oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^2$) may also be present. PCR reagents may optionally contain a template from which a target sequence can be amplified.

As used herein, the term "flap cleavage reaction" refers to a reaction in which a substrate is cleaved in an overlap-dependent manner by a flap endonuclease to release a flap. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447).

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable.

The term "enzymatic removing" refers to a covalent cleavage that is catalyzed by an enzyme (e.g., an exonuclease or endonuclease). Flap endonuclease, T7 exonuclease, exonuclease VII and apurinic/apyrimidinic (AP) endonuclease are examples of enzymes that can cleave nucleotides.

The term "nicking", as used herein, refers to a reaction that breaks the phosphodiester bond between two nucleotides in one strand of a double-stranded DNA molecule to produce a 3'-hydroxyl group and a 5' phosphate group.

The term "nick site", as used herein, refers to the site at which a double-stranded DNA molecule has been nicked.

The terms "nicking endonuclease" and "sequence-specific nicking restriction endonuclease" refer to an enzyme that nicks double-stranded DNA at a specific sequence to which the enzyme binds. Such an enzyme does not induce a double-stranded break at its binding site. Rather, a sequence-specific nicking restriction endonuclease catalyzes breakage of a phosphodiester bond in only one strand of a double-stranded DNA molecule.

The term "blocked", in the context of an oligonucleotide that is blocked at its 3' end when it is annealed to a target nucleic acid, refers to an oligonucleotide that cannot be extended by a template-dependent polymerase, either because the 3' end of the oligonucleotide has a non-natural nucleotide at the 3' end (e.g., by a dideoxy nucleotide or any of a multitude of nucleotides that are not substrates for the polymerase) or because the 3' end of the oligonucleotide is mis-matched with the target, i.e., because one or more nucleotides at the 3' end of the oligonucleotide are not complementary to correspondingly positioned nucleotides in the target sequence). In certain cases, blocked oligonucleotides cannot be digested by a 3' to 5' exonuclease, e.g., because one or more phosphodiester linkages has been altered to become, for example, a phosphothioate linkage.

The term "adjacent to" refers to a distance of less than the longest dimension of a nucleotide. The term "ligatably adjacent to" means that two nucleotides are immediately adjacent to one another on a strand with no intervening nucleotides.

Figure 1:
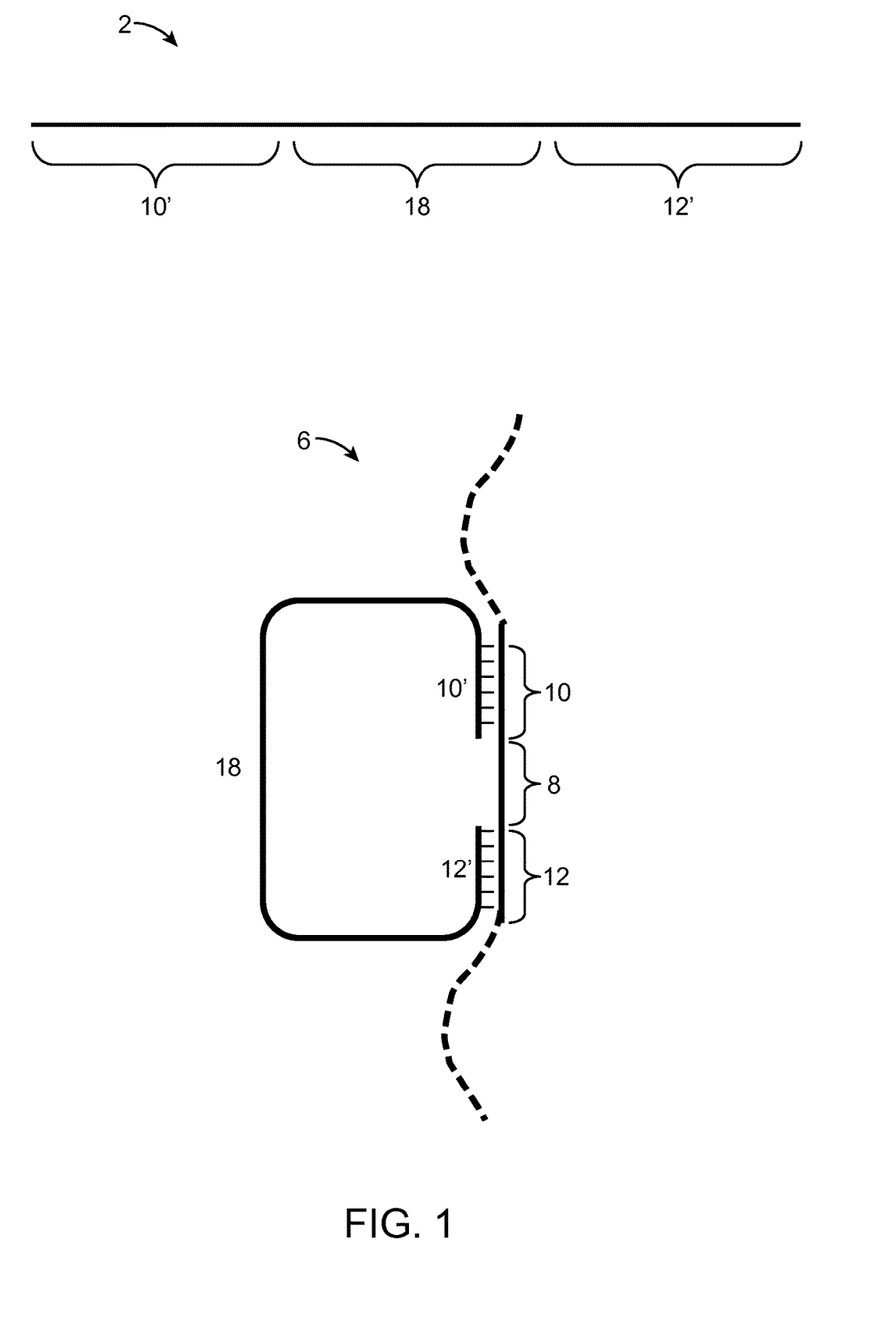
FIG. 1 schematically some of the features of a C-probe.

The term "C-probe" refers to a molecule illustrated in FIG. 1. With reference to FIG. 1, C-probe 2 contains an oligonucleotide sequence 18 (a sequence of defined length), first region 10' and second region 12', where the first region 10' hybridizes to a first genomic sequence 10 and the second region 12' hybridizes to a second genomic sequence 12. In a genome under study, the first genomic sequence and the second genomic sequence are on the same strand and they flank a target sequence 8 (a sequence that is to be enriched and optionally analyzed later in the protocol). FIG. 1 illustrates a complex 6 containing a C-probe and a target nucleic acid. A C-probe is called a C-probe because it forms a "C" shape when hybridizes to the target nucleic acid. In this complex, if the target nucleic acid is represented as a straight line, then the 5' and 3' ends of the C-probe face one another in the sense that if the 3' end of the C-probe could be extended by a polymerase, then the polymerase would run into the 5' end of the C-probe. In other words, in the complex formed by hybridizing a C-probe to a target nucleic acid, the ends of the C-probe are inverted relative to one another, as shown in FIG. 1A. A C-probe may be RNA, DNA or a combination of RNA and DNA, for example.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Figure 2A:
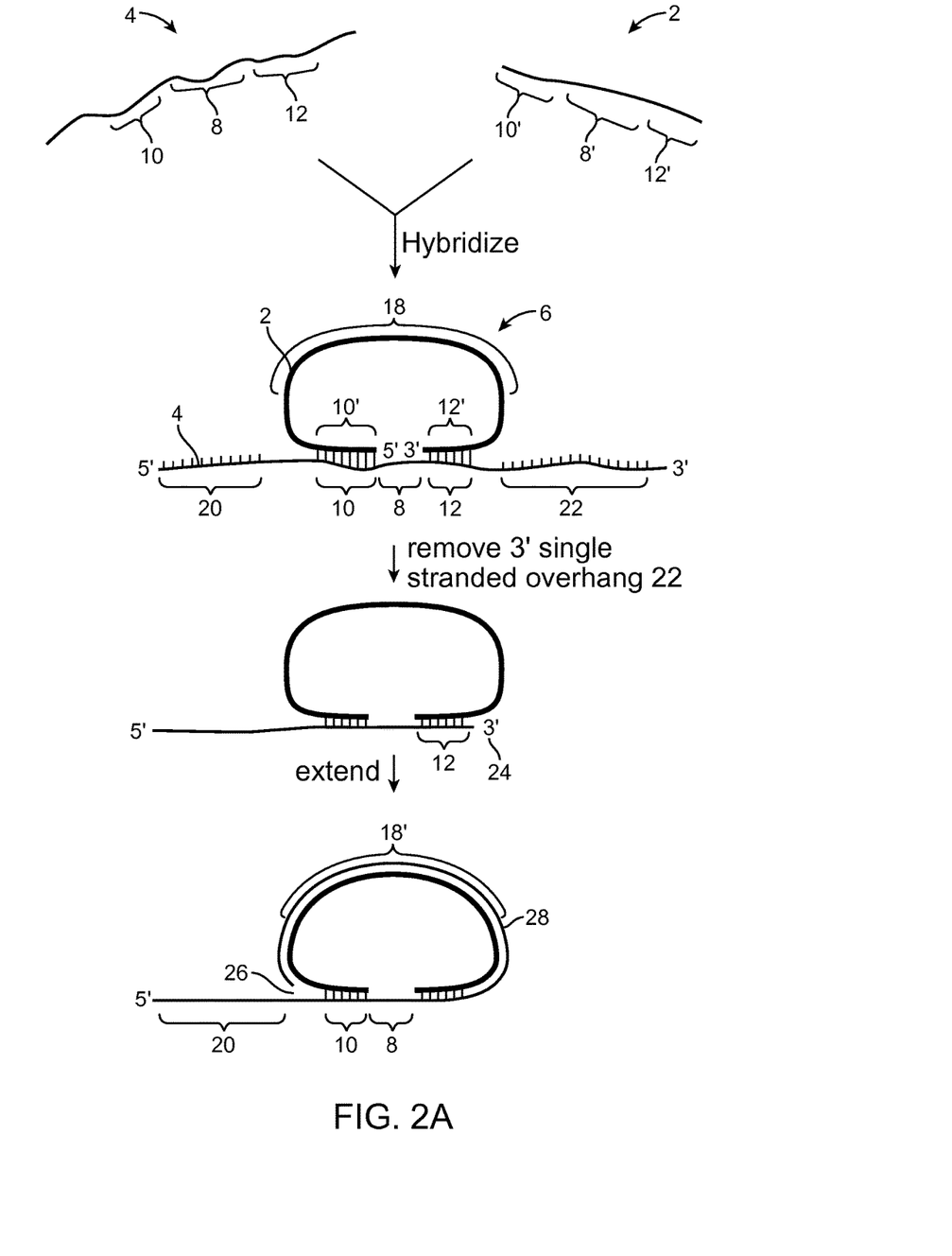
FIGS. 2A and 2B schematically some general features of a first embodiment of the method.

With reference to FIG. 2A, certain embodiments of the method involve hybridizing a C-probe 2 to a strand of a target nucleic acid 4 to produce complex 6, where: (i) strand 4 comprises target sequence 8 that is flanked by first sequence 10 and second sequence 12, and (ii) C-probe 2 comprises first region 10' that hybridizes to first sequence 10, second region 12' that hybridizes to second sequence 12, and an oligonucleotide sequence 18 between first region 10' and second region 12'. In C-probe 2, the lengths of region 10' and 12' may vary from 12 to 50 or more nucleotides and in certain embodiments may be in the range of 15 to 30 nucleotides in length. The length of oligonucleotide sequence 18 may also vary and, in certain cases, may be from 12 to 150 or more nucleotides in length, e.g., 15 to 100 nucleotides in length. The nucleotide sequence of oligonucleotide sequence 18 may vary in accordance with how that sequence is used later in the protocol. In some embodiments, oligonucleotide sequence 18 provides a binding site for at least one primer (e.g., binding sites for one or two or more primers and, in certain cases, a molecular barcode sequence). This binding site may be of at least 12 nucleotides in length (e.g., in the range of 13 to 50 nucleotides in length). Target sequence 8 may be of any length and in certain cases may be in the range of 10 nt to 1,000 nt in length, e.g., 100 nt to 800 nt in length.

After hybridizing C-probe 2 to target nucleic acid 4 to produce complex 6, the method comprises enzymatically removing the 3' overhanging end 22 from target nucleic acid 4 in complex 6. In this context the overhanging end 22 is the length of single-stranded nucleic acid that is 3' to the second region 12. The end that is cleaved from target nucleic acid 4 contains the 3' end of the target nucleic acid. This step results in a 3' hydroxyl group 24 that is at the 3' end of the second sequence 12. This step may be done by any suitable enzyme, including T4 polymerase (in the presence of dNTPs), where the exonuclease activity of the enzyme trims the single stranded DNA. Exonuclease I, exonuclease T, exonuclease V may also be employed.

In particular, exonuclease T may be used to trim the 3' end of the target nucleic acid 4, since it has been shown to efficiently create blunt ends of double-stranded DNA targets containing a 3' overhang (Zuo and Deutscher, Nucl. Acids Res. (1999) 27: 4077-4082) Alternatively, in cases where the overhanging end 22 is expected to be long, Exonuclease I may be used, as this enzyme is highly processive. However, in cases where Exonuclease I is used, it may be used in the presence of another enzyme with 3' to 5' exonuclease activity, such as T4 polymerase in the presence of dNTPs.

After the 3' end of the target nucleic acid has been trimmed to produce 3' hydroxyl group 24, the 3' end of the first sequence is extended using the C-probe as a template. This step may be done using the same enzyme as used in the prior step (e.g., T4 polymerase) or another template-dependent polymerase in the presence of nucleotides. If the C-probe is RNA, then a reverse transcriptase can be used. Depending on how the method is implemented, the template-dependent polymerase may or may not be a strand-displacing polymerase. This extending step produces an extension product 28 comprising the complement 18' of oligonucleotide sequence 18 and a 3' hydroxyl group 26 that is adjacent to the 5' end of the first sequence 10, i.e., at a position that base-pairs to the nucleotide that is immediately 5' to the 5' end of the first sequence 10. In certain cases, the 3' end of the C-probe is blocked in order to prevent extension of the C-probe using the target nucleic acid as a template. In these embodiments, the 3' end of the C-probe may comprises a dideoxy nucleotide and a phosphothioate linkage (to prevent exonuclease digestion).

Figure 2B:
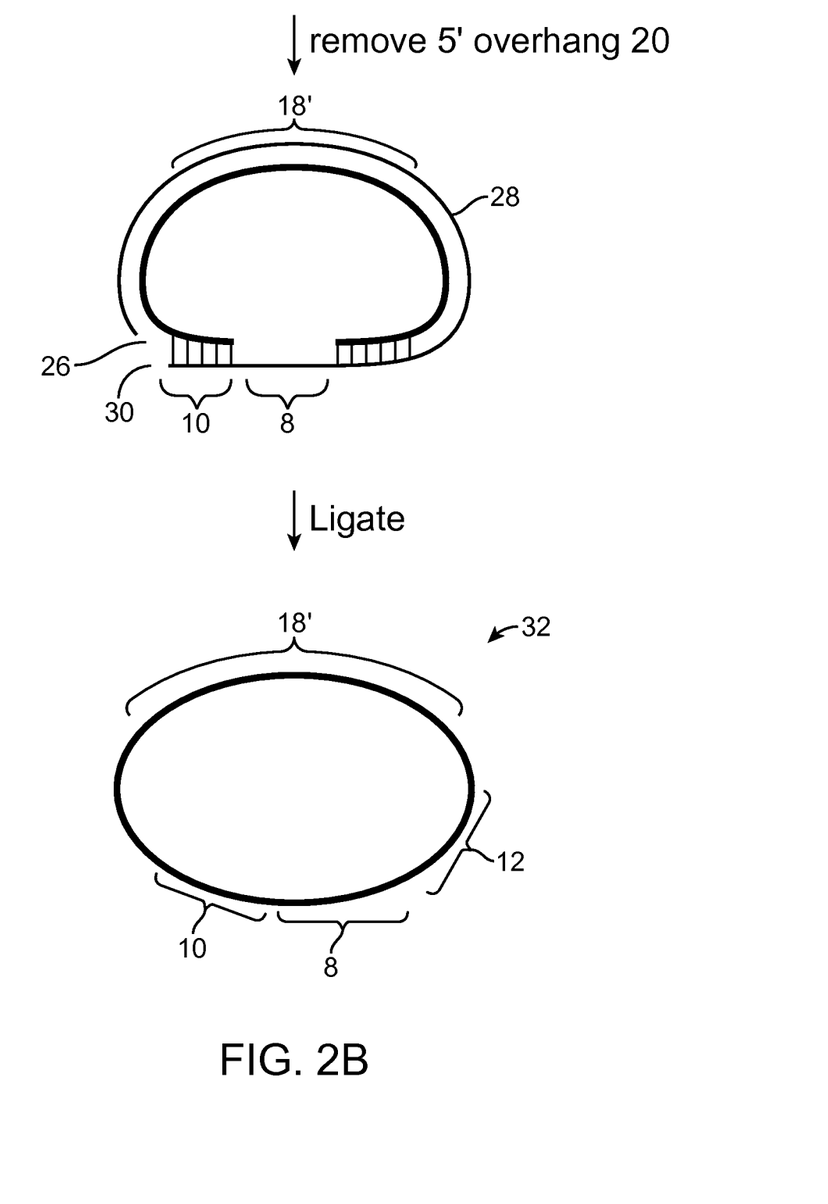

The method also comprises enzymatically removing the 5' overhanging end 20 from the target nucleic acid, either before or after the extending step described above, to produce a 5' phosphate group 30 at the 5' end of the first sequence 10 (shown on FIG. 2B). This step results in a complex in which the 5' end of the first sequence is ligatably adjacent to the 3' end of extension product 28. The 5' overhanging end 20 may be removed by a variety of enzymes, including Lambda exonuclease, RecJ exonuclease, or T7 exonuclease. Lambda exonuclease may be used in cases where the 5' overhanging end 20 contains a 5' phosphate group, for example, if the target DNA fragment 4 is created by digestion with a restriction endonuclease. RecJ exonuclease may be preferred in cases where the target DNA fragment 4 does not contain a 5' phosphate, and where the extension step comprises a FEN activity, as RecJ may leave 5' overhangs or flaps.

Figure 5:
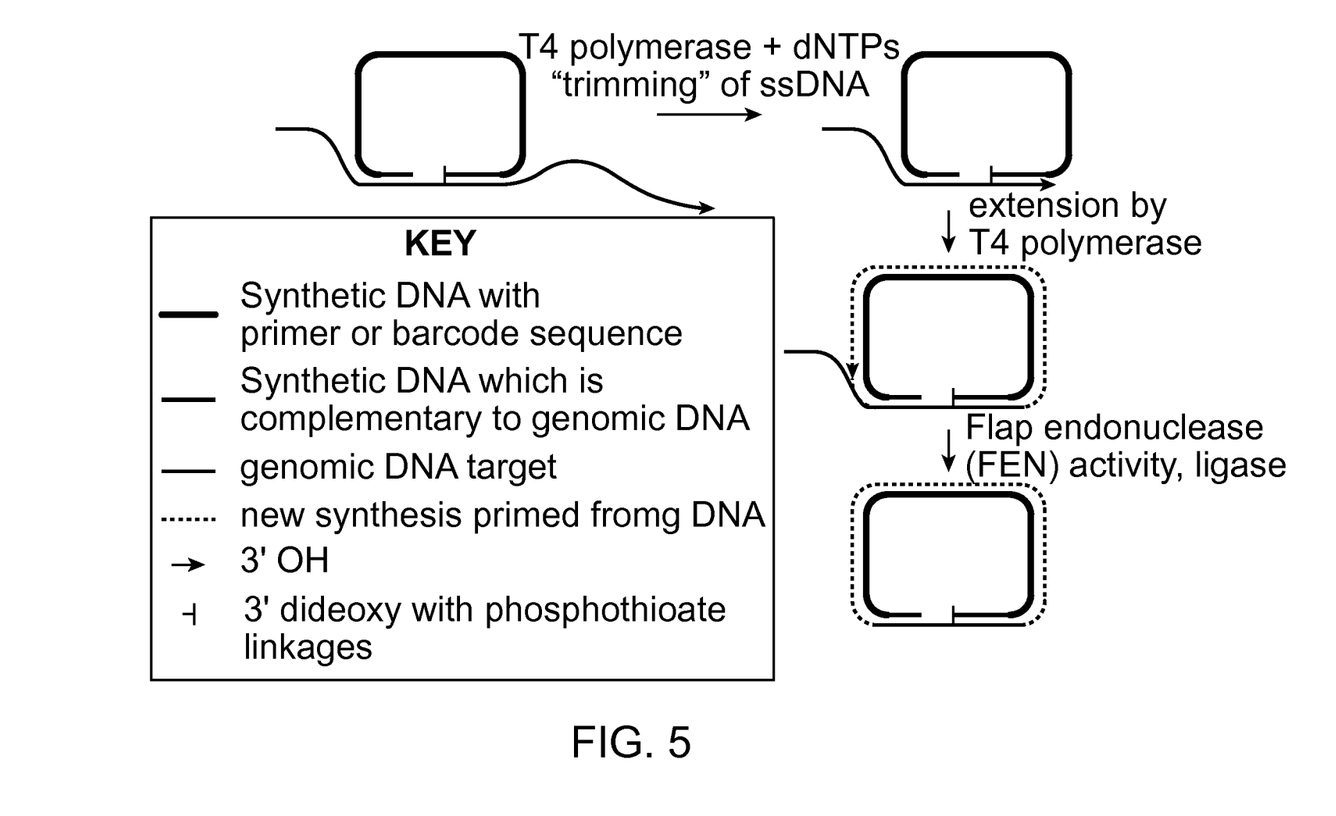
FIG. 5 schematically illustrates one implementation of the method.

As noted above, enzymatically removing the 5' overhanging end 20 from the target nucleic acid can be done before the extending step or after the extending step. In the embodiment shown in FIGS. 2A and 2B, the 5' overhanging end is removed after the extending step. In this embodiment, the complex produced by extending the 3' end 12 using C-probe 2 as a template contains an overlap that can be cleaved by a flap endonuclease. As such, in the embodiment shown in FIGS. 2A and 2B, the 5' overhanging end 20 may be removed using a flap endonuclease. Flap endonuclease activities may be provided by enzymes including but not limited to human FEN-1, Cleavase enzyme described by Third Wave Technologies, or the FEN activity of Taq polymerase. FIG. 5 illustrates an implementation of this method in which the 3' overhanging end of the target nucleic acid is enzymatically removed by the exonuclease activity of T4 DNA polymerase; the extending step is done using the polymerase activity of T4 DNA polymerase; and the 3' overhanging end of the target nucleic acid is enzymatically removed by a flap endonuclease.

Figure 3:
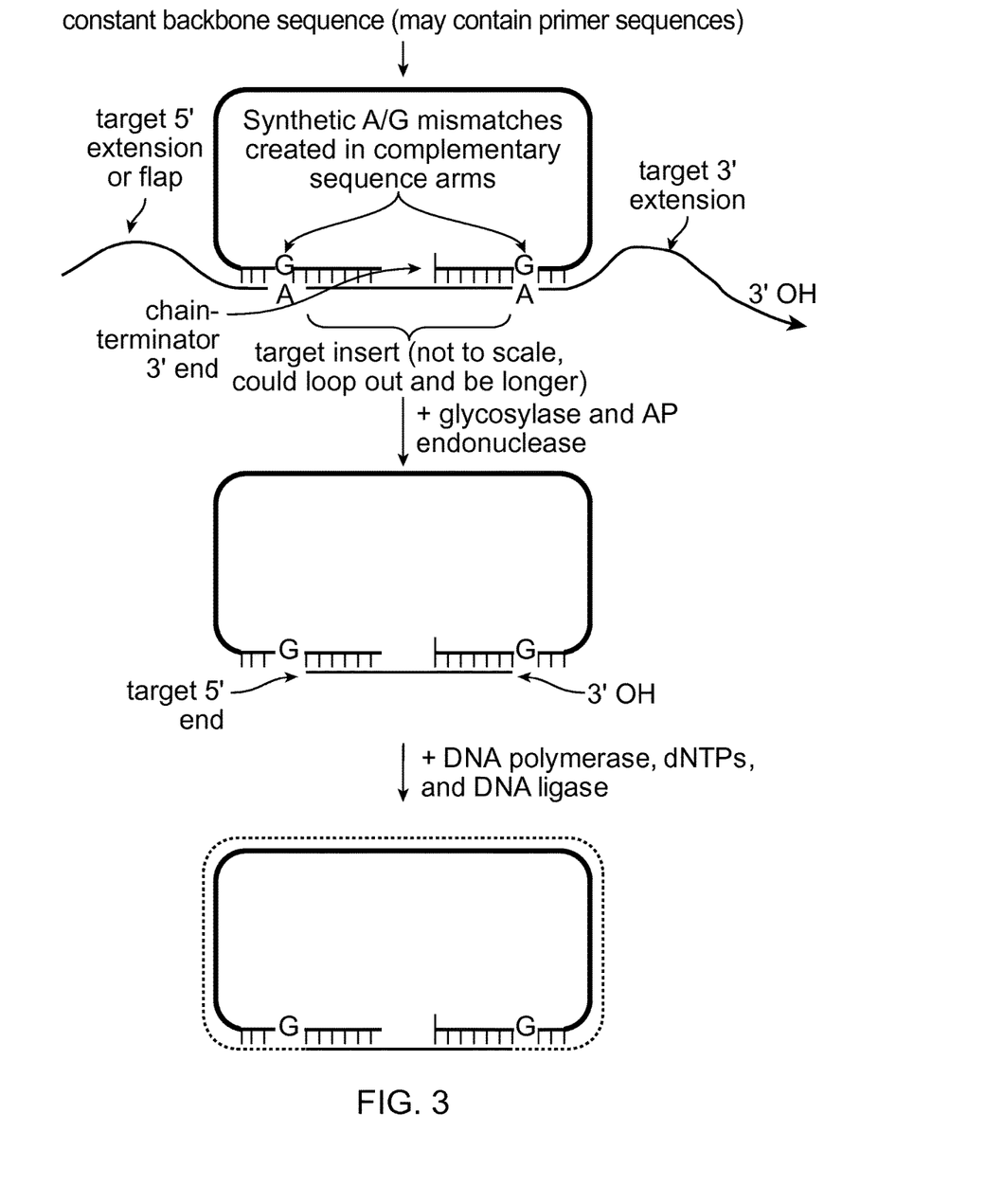
FIG. 3 schematically illustrates one way in which the 3' and 5' overhangs can be removed using glycosylase and AP endonuclease.

In other embodiments, the 5' overhanging end can be removed before the extending step, e.g., at the same time at which the 3' overhanging end is removed. In some embodiments, the 3' and 5' overhanging ends of the target nucleic acid may be simultaneously enzymatically removed using a single-strand specific bi-directional exonuclease, e.g., exonuclease VII, in the optional presence of a polymerase to fill in any ends that have been excessively digested. In alternative embodiments, a cocktail containing a 3' to 5' exonuclease (such as exonuclease I, exonuclease T or exonuclease V) and a 5' to 3' exonuclease (e.g., T7 exonuclease) may be used. In one embodiment and as illustrated in FIG. 3, the C-probe may be designed to provide G-A mismatches when it is hybridized to the target nucleic acid. In this embodiment, the 3' and 5' overhanging ends of the target nucleic acid can be enzymatically removed using a glycosylase and AP endonuclease (see, e.g., Howell et al Nuc. Acids Rs. 2010 38 e99). In this embodiment, a combination of MutY glycosylase and AP-endonuclease activities (which may be provided by a single enzyme or two enzymes) can be used to specifically cleave a double-stranded DNA at a G-A mismatch. In a preferred embodiment, MutY glycosylase may be used used in combination with endonuclease IV. If a G is provided in one of the complementary sequences in the C-probe at a position that result in a mismatch with an A in the target nucleic acid, then a G-A mismatch will be produced. After processing by the glycosylase and AP-endonuclease activities, the genomic DNA target will have a 3' end that can be extended around the C-probe, as shown in FIG. 1A. This embodiment eliminates the need for a 3' to 5' exonuclease to create the 3' end. Further, both of the complementary sequences could be designed to create G-A mismatches at a position that is occupied by an A in the target nucleic acid. In this embodiment, the glycosylase and AP-endonuclease activity can replace the 3' to 5' exonuclease and flap endonuclease activities. In this embodiment, only the glycosylase and AP-endonuclease activity, a suitable polymerase and a DNA ligase may be all that is needed to perform the method.

Figure 6:
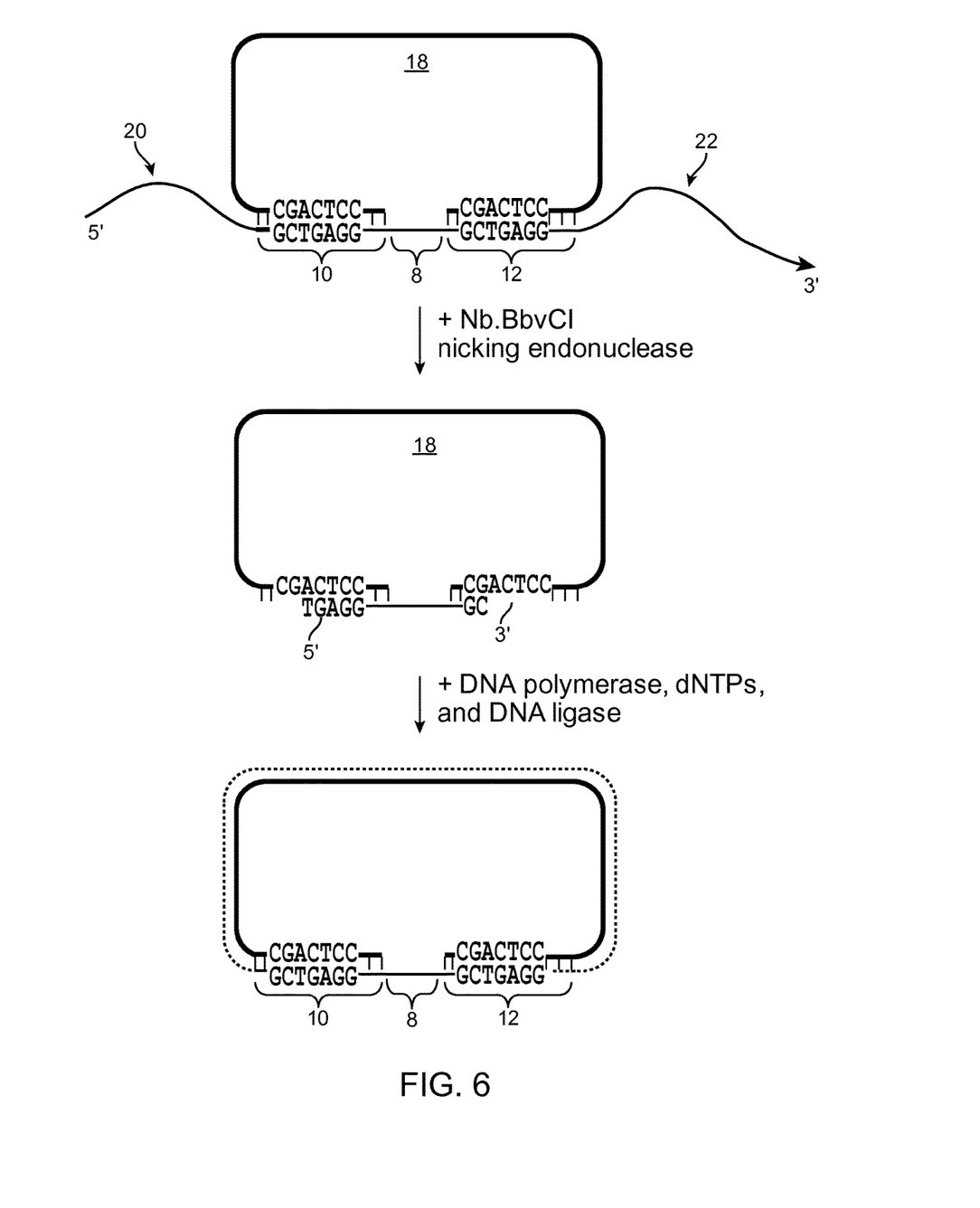
FIG. 6 schematically illustrates one way in which the 3' and 5' overhangs can be removed using a nicking endonuclease.

In other embodiments and as shown in FIG. 6, a nicking endonuclease activity may be used to remove either the 5' overhanging end 20, the 3' overhanging end 22, or both ends. In these embodiments, the target sequences 10 and 12 are chosen to contain recognition sites for a nicking endonuclease, such that the nicking endonuclease activity will cleave either strand 10 or strand 12 without cleaving the complementary strands 10' and 12' in the C-probe. A number of suitable enzymes are known in the art. For example, the enzyme Nb.BbvCI cleaves between the C and T residues in the sequence 5' GCTGAGG 3', which could be included in the target sequence 10 or 12, but Nb.BbvCI will not cleave in the complementary sequence 5' CCTCAGC 3' in the C-probe sequence 10' or 12'. In these embodiments the cleaved overhanging ends 20 and 22 will diffuse away, leaving a free 3' hydroxyl group at the cleavage site in 12 and a 5' phosphate group in the cleavage site in 10. Either the same nicking endonuclease endonuclease could be used for both target sequences 10 or 12, or different nicking endonucleases may be used for target sequences 10 or 12. In addition, a library of C-probes may contain individual C-probes with 0, 1, or 2 nicking endonuclease sequences, according to the context of the target sequences 8.

After the 5' overhanging end as been removed and as shown in FIG. 2B, the method further comprises ligating 5' phosphate group 30 at the 5' end of the first sequence 10 to the 3' hydroxyl group 26 to produce a covalently closed circular DNA molecule 32 that contains the target sequence 8 and the complement of the oligonucleotide sequence 18'. As shown in FIG. 2B, closed circular DNA molecule 32 is shown without the C-probe hybridized to it. If necessary, the C-probe can be separated from the circular DNA molecule 32 by any convenient method. For example, the C-probe could be biotinylated and the C-probe could be removed by denaturing the complex and then binding to the C-probe to streptavidin. In an alternative embodiment, the complex could be denatured, and treated with an exonuclease that is specific for single stranded DNA. Such an exonuclease would digest the linear DNA, while leaving the circular DNA intact. In an alternative embodiment, the C-probe could be prepared using deoxyuracil in place of deoxythymidine, and the mixture could be treated with USER enzyme to cleave the DNA containing uracils, as described by New England Biolabs (see, e.g., U.S. Pat. No. 7,435,572). Finally, if the C-probe is RNA, the C-probe may be digested using NaOH or by RNAse treatment, although any suitable digestion method may be used.

In any of the above embodiments, the initial target nucleic acid fragment can in certain cases be produced from genomic DNA using chemical, physical or transposase-catalyzed fragmentation methods, see, e.g., Adey et al (Genome Biology 2010, 11:R119). For example, the physical fragmentation methods may sonication, nebulization, or shearing of genomic DNA. In certain embodiments, prior to performing the method, the genomic DNA may be fragmented to an average size in the range of 100 bp to 10 kb, e.g., 200 bp to 1 kb. In embodiments, the average size range may be chosen to match the characteristics of the enzymes used in the method. For example, if a less-processive exonuclease or flap endonuclease is used to cleave overhanging ends 20 and 22, one may fragment the genomic DNA to a shorter target length, for example, 100 bp to 300 bp. Alternatively, if the C probes are designed to capture longer target sequences 8, it may be preferable to start with genomic DNA fragmented to a longer target length, for example, 300 bp to 1 kb or more.

In one embodiment, the region extended in the extending step described above is composed of no more than three different nucleotides. In these embodiments, oligonucleotide sequence 18 may be constructed with fewer than 4 nucleotides (e.g., A, C, G but not T). In this embodiment, the polymerase with a 5' to 3' exonuclease activity could be used (which may also have FEN activity), without digesting and reading through the target sequence. In this example, a 3' to 5' exonuclease activity will process the 3' overhang of the target nucleic acid back to the duplex region, leaving a 3'-hydroxyl that can be extended by the polymerase. The polymerase can extend the 3'-hydroxyl using the oligonucleotide sequence as a template, adding dT, dC and dG nucleotides. When the polymerase extends around the C-probe and reaches the target nucleic acid, it creates a flap substrate that can be cleaved by a flap endonuclease. Some polymerases, e.g., Taq, possess inherent flap endonuclease activity and will remove the 5' flap. In this case, the polymerase will stall at the first T residue in the target because no dATP is present in the reaction mix.

In some embodiments, the method may further comprise: (f) amplifying the target sequence from said circular DNA molecule using one or more primers that either hybridize with or have the same sequence as sites in the oligonucleotide sequence. The method may further involve (g) sequencing the amplification product of (f) to provide the nucleotide sequence of at least part of the target sequence.

In some embodiments, the method may further comprise steps to detect CpG methylation or other DNA modifications in the target sequence. For example, an antibody against 5-methylcytosine could be applied to the closed circular DNA molecule 32 in a protocol to enrich sequences containing 5-methylcytosine. Alternatively, the closed circular DNA molecule 32 could be digested with a restriction enzyme which is sensitive to CpG methylation. Many such methods are known in the art. In these ways methylation status of the target sequence 8 could be compared from different samples.

Figure 4:
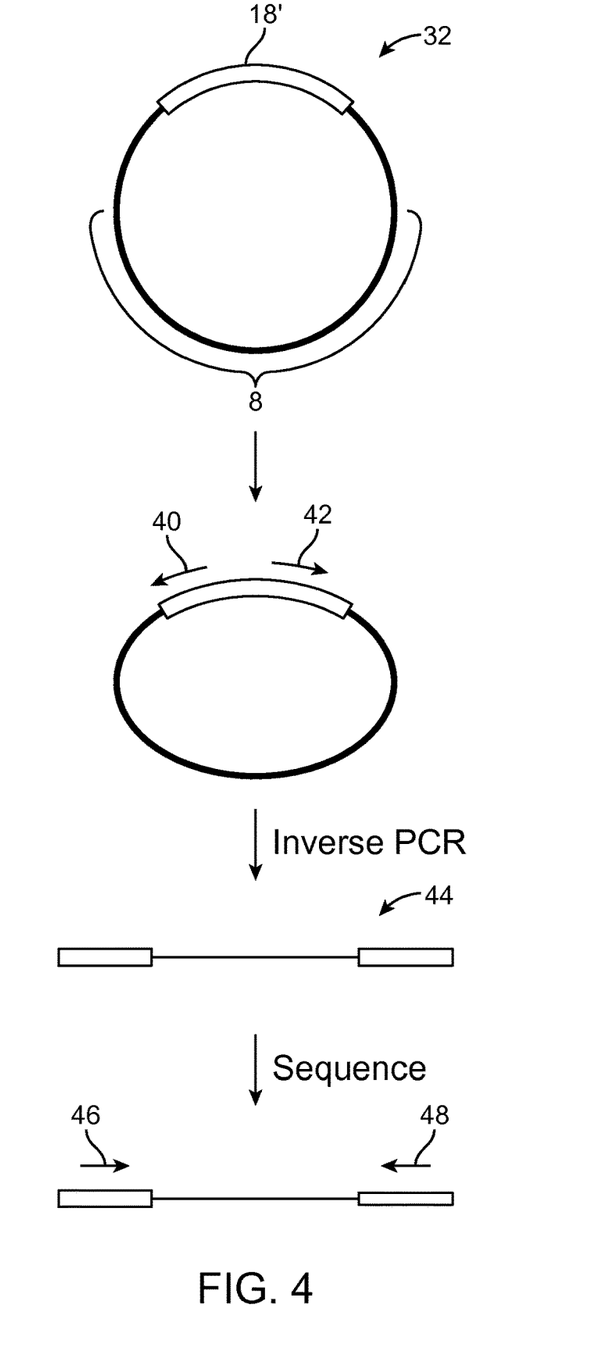
FIG. 4 schematically illustrates one way in which a target sequence can be amplified and sequenced.

FIG. 4 schematically illustrates a way in which the target sequence can be amplified and sequenced. As illustrated in FIG. 4, the product DNA molecule 32 (which comprises the target sequence 8 and the complement of oligonucleotide sequence 18'), may be amplified using inverse PCR primers 40 and 42 that bind to sites that are provided by the C-probe. Amplification product 44 may be sequenced to provide the nucleotide sequence of at least part of the target sequence. In certain cases, the sequencing may be done using primers 46 and 48 that hybridize to sequencing primer sites the C-probe. In alternative embodiments, the target sequence can be amplified by rolling circle amplification (RCA). In these embodiments, the amplification product will comprise a linear concatemer of the complement to the closed circular DNA molecule 32.

As would be apparent, in certain embodiments, the sequences added by the C-probe may contain sequences that are compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol. Biol. 2009; 553:79-108); Appleby et al (Methods Mol. Biol. 2009; 513:19-39) and Morozova (Genomics. 2008 92:255-64), which are incorporated by reference for the general descriptions of the methods and the particular steps of the methods, including all starting products, reagents, and final products for each of the steps. The sequences may be present in the oligonucleotide sequence of the C-probe. In certain cases, oligonucleotide sequence part of the C-probe may contain two sets of primer binding sites, one for amplifying the circular DNA by inverse PCR, and the other for sequencing the resultant product.

The oligonucleotide sequence of the C-probe may also contain a molecular barcode, positioned downstream of the amplification and sequencing primer binding sites, that can be used to identify from which sample a sequence is derived, or to count how many different starting molecules have been sequenced. In other embodiments, the amplicon may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. Pat Appln Nos. 2006003171 and 20090029477. Nanopore sequencing technologies that are suited to read long stretches of DNA could be used to sequence concatemers created by rolling circle amplification of the closed circular DNA molecule 32.

The lengths of the various regions of a subject C-probe may vary greatly depending upon the desired application and how much freight (i.e., how many primer binding sites, barcodes, etc.) are carried by the one or more second oligonucleotides. In certain embodiments, the oligonucleotide sequence of the C-probe may be of 20-100 base pairs (e.g., 30 bp to 60 bp) in length, and the sequences of the flanking regions (which specifically hybridize to a target fragment in a genome) may be of 10 to 100 bases (e.g., 12-50 bases) in length. As should be readily apparent, the nucleotide sequence of the oligonucleotide sequence part of the C-probe should be designed to that it does not have sufficient homology to allow significant hybridization to the genome under study.

The method described above can be employed to manipulate and analyze DNA from virtually any nucleic acid source, including but not limited to genomic DNA and complementary DNA, plasmid DNA, mitochondrial DNA, synthetic DNA, and BAC clones etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the initial DNA used in the method may be derived from a mammal, where in certain embodiments the mammal is a human.

In certain embodiments, the initial DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed. In addition, the reaction may be multiplex such that a plurality of different target loci (e.g., 10 to 1000) are targeted in a single reaction. In these embodiments, the ends of the C-probes (i.e., the regions that hybridize to the target sequences may vary, whereas the central oligonucleotide sequence may be the same for all of the C-probes. In these embodiments, ends of the C-probes may be $T_m$-matched in that their $T_m$s that are within a defined range, e.g. ±5° C., ±10° C., or ±15° C.

Kits

Also provided by this disclosure are kits for practicing the subject method, as described above. The subject kits contain at least a C-probe as described, as well as suitable reaction reagents (e.g., buffers etc.) for performing the method. The various components of the kit may be present in separate containers or certain compatible components may be pre-combined into a single container, as desired. In some embodiments, the kit may comprise a C-probe comprising a first region that hybridizes to the first sequence in a strand of a target nucleic acid, a second region that hybridizes to the second sequence in the strand, and an oligonucleotide sequence between the first and second regions, as described above. In many cases, the 3' end of the C-probe is blocked. In addition to the probe, the kit may contain any of the additional components used in the method described above, e.g., one or more enzymes that remove 5' and 3' single stranded overhangs, DNA ligase, and a DNA polymerase, etc.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The invention claimed is:

1. A method of processing a nucleic acid, comprising:
   (a) hybridizing a C-probe to a strand of a target nucleic acid to produce a complex, wherein:
      (i) said strand comprises a target sequence that is flanked by a first sequence and a second sequence, and (ii) said C-probe comprises a first region that hybridizes to said first sequence, a second region that hybridizes to said second sequence, and an oligonucleotide sequence between said first and second regions, (b) enzymatically removing any 3' overhang from the target nucleic acid of said complex to produce a 3' hydroxyl group at the 3' end of said first sequence;

(c) extending the 3' end of said first sequence using the oligonucleotide sequence of said C-probe as a template, wherein said extending results in a 3' hydroxyl group that is adjacent to the 5' end of said second sequence;

(d) enzymatically removing any 5' overhanging from the target nucleic acid, either before or after said extending of step (c), to produce a 5' phosphate group at the end of said second sequence; and (e) ligating the 5' phosphate group at the end of the second sequence to the 3' hydroxyl group that is adjacent to the 5' end of said second sequence to produce a circular DNA molecule that contains said target sequence and the complement of said oligonucleotide sequence.

2. The method of claim 1, wherein said method comprises:

(f) amplifying the target sequence from said circular DNA molecule using one or more primers that either hybridize with or have the same sequence as sites in the oligonucleotide sequence.

3. The method of claim 2, further comprising:

(g) sequencing the amplification product of (f) to provide the nucleotide sequence of at least part of the target sequence.

4. The method of claim 1, wherein the 5' overhanging end of the target nucleic acid is enzymatically removed before step (c).

5. The method of claim 4, wherein the 3' and 5' overhanging ends of the target nucleic acid are enzymatically removed using a single-strand specific bi-directional exonuclease, optionally in the presence of a polymerase.

6. The method of claim 5, wherein said single-strand specific bi-directional exonuclease is exonuclease VII.

7. The method of claim 4, wherein said C-probe is designed to provide G-A mismatches in the complex, and the 3' and 5' overhanging ends of the target nucleic acid are enzymatically removed using glycosylase and AP endonuclease activities.

8. The method of claim 4, wherein the 3' and 5' overhanging ends of the target nucleic acid are enzymatically removed using exonuclease T and T7 exonuclease.

9. The method of claim 1, wherein the 5' overhanging end of the target nucleic acid is enzymatically removed after step (c).

10. The method of claim 1, wherein:
the 3' overhanging end of the target nucleic acid is enzymatically removed by the exonuclease activity of T4 DNA polymerase;
said extending step (c) is done using the polymerase activity of T4 DNA polymerase; and
the 3' overhanging end of the target nucleic acid is enzymatically removed by a flap endonuclease.

11. The method of claim 1, wherein the oligonucleotide sequence comprises a molecular barcode.

12. The method of claim 1, wherein said target nucleic acid is genomic DNA.

13. The method of claim 12, wherein the genomic DNA is randomly sheared genomic DNA that has been produced using a chemical, physical or transposase-catalyzed fragmentation method.

14. The method of claim 1, wherein the 3' overhanging end of the target nucleic acid is enzymatically removed by a nicking endonuclease.

15. The method of claim 1, wherein the 5' overhanging end of the target nucleic acid is enzymatically removed by a nicking endonuclease.

16. The method of claim 1, wherein said target sequence is in the range of 10 nt to 1,000 nt in length.

17. The method of claim 1, wherein the region extended in step (c) is composed of no more than three different nucleotides.

18. The method of claim 1, wherein the 3' end of said C-probe is blocked to prevent the addition of nucleotides by a polymerase or a ligase.

19. The method of claim 18, wherein the 3' end of said C-probe comprises a dideoxy nucleotide and a phosphothioate linkage.

20. A kit for processing a target nucleic acid, comprising:
a C-probe comprising a first region that hybridizes to a first sequence in a strand of said target nucleic acid, a second region that hybridizes to a second sequence in said strand, and an oligonucleotide sequence between said first and second regions, wherein the 3' end of said C-probe is blocked to prevent the addition of nucleotides by a polymerase or a ligase,
one or more enzymes that remove 5' and 3' single stranded overhangs; and
a DNA ligase.

* * * * *

UNITED STATES PATENT AND TRADEMARK OFFICE
CERTIFICATE OF CORRECTION

PATENT NO. : 10,150,960 B2
APPLICATION NO. : 13/777842
DATED : December 11, 2018
INVENTOR(S) : Brian Jon Peter Page 1 of 1

It is certified that error appears in the above-identified patent and that said Letters Patent is hereby corrected as shown below:

In the Drawings

On sheet 6 of 7, in Figure 5, Line 10, delete "fromg" and insert -- from --, therefor.

In the Specification

In Column 2, Line 8, delete "2D" and insert -- $2^{ND}$ --, therefor.

In Column 2, Line 40, delete "then" and insert -- than --, therefor.

In Column 8, Line 54, delete "$Mg^2$)" and insert -- $Mg^{2+}$) --, therefor.

In Column 11, Line 31, delete "-4082)" and insert -- -4082). --, therefor.

In Column 12, Line 49, delete "used used" and insert -- used --, therefor.

In Column 13, Line 16, delete "endonuclease endonuclease" and insert -- endonuclease --, therefor.

In Column 13, Line 22, delete "as" and insert -- has --, therefor.

In Column 15, Line 31, delete "Pat Appln Nos." and insert -- Pub. Nos. --, therefor.

Signed and Sealed this
Ninth Day of July, 2019

Andrei Iancu
*Director of the United States Patent and Trademark Office*